United States Patent [19]

Olesen et al.

[11] Patent Number: 5,200,422

[45] Date of Patent: Apr. 6, 1993

[54] BENZIMIDAZOLE DERIVATIVES, THEIR PREPARATION AND USE

[75] Inventors: Soren-Peter Olesen, Bronshoj; Frank Wätjen, Herlev, both of Denmark

[73] Assignee: NeuroSearch A/S, Glostrup, Denmark

[21] Appl. No.: 731,412

[22] Filed: Jul. 17, 1991

Related U.S. Application Data

[63] Continuation-in-part of Ser. No. 586,900, Sep. 24, 1990, abandoned.

[51] Int. Cl.$^5$ ................ A61K 31/415; C07D 487/00; C07D 235/04
[52] U.S. Cl. .................................. 514/387; 514/388; 548/306.4; 548/307.1; 548/307.4
[58] Field of Search ................ 548/305, 306; 514/387, 514/388

[56] References Cited

U.S. PATENT DOCUMENTS 3,338,916  8/1967  Hunziker et al. .................... 548/305

OTHER PUBLICATIONS

Small et al., K+-channel opening as a mechanism for relaxing airways smooth muscle in New Anti-Asthma Drugs (pp. 89-94) 1988 Birkhäuser Verlag Basel.
Dr. S. G. Dilly, Cromakalim/Lemakalim, experience in hypertension and nocturnal asthma in Conference Documentation, Potassium Channels '90, The Royal College of Physicians, Dec. 6-7, 1990.
Neuroscience Letters 115, 195-200 (1990).
Neuroscience 37(1), 55-60 (1990).
The Journal of Pharmacology and Experimental Therapeutics 251(1), 98-104 (1989).
Leo H. Sternbach, "The Benzodiazepine Story", J. Med. Chem 22(1), 1-7 (1979).
U. Schacht et al., Drug Development Research Supplement 1, 83-93 (1982).
W. Sleghart et al., Biochemical Pharmacology 33(24) 4033-4038 (1984).
W. E. Müller et al., Pharmacopsychiat. 19, 314-315 (1986).
Bianchi et al. in Eur. J. Med. Chem.—Chimica Therapeutica 16(4), 321-326 (1981).
Clark et al. in J. Med. Chem. 21 (9), 965-978 (1978).
European Journal of Pharmacology 167, 181-183 (1989).

Primary Examiner—Nicholas S. Rizzo
Assistant Examiner—Matthew V. Grumbling
Attorney, Agent, or Firm—Gordon W. Hueschen

[57] ABSTRACT

A compound having the formula

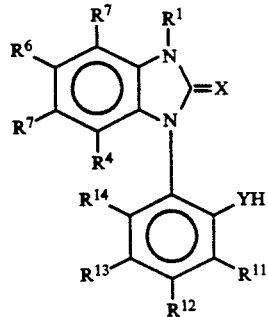

wherein $R^1$ is hydrogen, $NH_2$ or $C_{1-6}$-alkyl which may be branched;
X is O, S, NCN;
Y is O, S;
$R^4$, $R^5$, $R^6$ and $R^7$ independently of each other are hydrogen, halogen, $CF_3$, $NO_2$, $NH_2$, OH, $C_{1-6}$-alkoxy, C(=O)-phenyl or $SO_2NR^IR^{II}$ wherein $R^I$ and $R^{II}$ independently are hydrogen or $C_{1-6}$-alkyl;
$R^{11}$ is hydrogen, halogen, $NO_2$ or $SO_2NR'R''$ wherein $R'$ and $R''$ independently are hydrogen or $C_{1-6}$-alkyl;
$R^{13}$ is hydrogen, halogen, phenyl, $CF_3$, $NO_2$;
$R^{12}$ is hydrogen or together with $R^{13}$ forms a $C_{4-7}$-carbocyclic ring which may be aromatic or partially saturated;
$R^{14}$ is hydrogen or together with $R^{13}$ forms a $C_{4-7}$-carbocyclic ring which may be aromatic or partially saturated;
pharmaceutical compositions thereof,
and a method of treating a disease in a mammal, including a human, responsive to opening of potassium channels, which comprises administering to a mammal in need thereof an effective amount of a compound as first above indicated, are disclosed.

8 Claims, No Drawings

BENZIMIDAZOLE DERIVATIVES, THEIR PREPARATION AND USE

The present application is a Continuation-in-Part of copending US patent application Ser. No. 07/586,900 which was filed Sep. 24, 1990, now abandoned.

The present invention relates to novel benzimidazole derivatives, a method of preparing the same, a method of treatment with the novel benzimidazole derivatives, and to pharmaceutical compositions comprising the same.

OBJECT OF THE INVENTION

It is an object of the present invention to provide novel benzimidazole compounds which are useful in the treatment of diseases in mammals, including a human, and especially in the treatment of diseases which can be treated by opening cell membrane potassium channels of such mammal.

Another object of the present invention is to provide a method of treating diseases in mammals, including a human, responsive to opening of potassium channels which comprises administering to a mammal in need thereof a compound of the invention.

A third object of the present invention is to provide novel pharmaceutical compositions for the treatment of diseases in mammals, including a human, responsive to the opening of potassium channels.

BACKGROUND OF THE INVENTION

Bianchi et al. in Eur. J. Med. Chem.—Chimica Therapeutica 16(4), 321-326 (1981) discloses benzimidazolin-2-on derivatives having anti-ulcer and antisecretory activity.

Clark et al. in J. Med. Chem. 21(9), 965-978 (1978) discloses imidazo[4,5-b]pyridin-2-on derivatives having analgesic activity.

It is generally well known that opening of potassium (K+) channels leads to a hyperpolarization and relaxation of cells. The presently known K+ channel openers (cromakalim and pinacidil for example) exert their effect primarily via the ATP sensitive K+ channel. They have a high affinity for vascular smooth muscle cells and are thus mostly vasodilators. Recent studies indicate, however, that K+ channel openers hyperpolarizing neuronal cells also have anticonvulsive and antiischemic effects in the central nervous system (the CNS) (European Journal of Pharmacology 167, 181-183 (1989), Neuroscience Letters 115, 195-200 (1990), Neuroscience 37(1), 55-60 (1990), The Journal of Pharmacology and Experimental Therapeutics 251(1), 98-104 (1989)). Furthermore recent studies demonstrate that potassium channel openers acting on airways smooth muscle (tracheal smooth muscle) cells will have anti-asthmatic effects (Small et al., K+-channel opening as a mechanism for relaxing airways smooth muscle in New Anti-Asthma Drugs (pp 89-94) 1988 Birkhäuser Verlag Basel, and Dr. S. G. Dilly, Cromakalim/Lemakalim, experience in hypertension and nocturnal asthma in Conference Documentation, Potassium Channels '90, The Royal College of Physicians, Dec. 6-7, 1990).

SUMMARY OF THE INVENTION

The invention then, inter alia, comprises the following, alone or in combination:

A compound having the formula

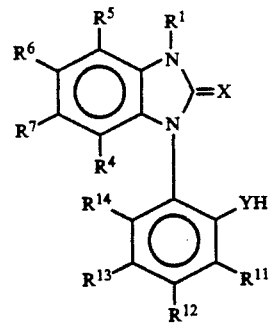

wherein $R^1$ is hydrogen, $NH_2$ or $C_{1-6}$-alkyl which may be branched;

X is O, S, NCN;

Y is O, S;

$R^4$, $R^5$, $R^6$ and $R^7$ independently of each other are hydrogen, halogen, $CF_3$, $NO_2$, $NH_2$, OH, $C_{1-6}$-alkoxy, C(=O)-phenyl or $SO_2NR^{I}R^{II}$ wherein $R^{I}$ and $R^{II}$ independently are hydrogen or $C_{1-6}$-alkyl;

$R^{11}$ is hydrogen, halogen, $NO_2$ or $SO_2NR'R''$ wherein R' and R'' independently are hydrogen or $C_{1-6}$-alkyl;

$R^{13}$ is hydrogen, halogen, phenyl, $CF_3$, $NO_2$;

$R^{12}$ is hydrogen or together with $R^{13}$ forms a $C_{4-7}$-carbocyclic ring which may be aromatic or partially saturated;

$R^{14}$ is hydrogen or together with $R^{13}$ forms a $C_{4-7}$-carbocyclic ring which may be aromatic or partially saturated;

and a compound as above which is 5-trifluoromethyl-2,3-dihydro-1-(5-chloro-2-hydroxyphenyl)-1H-2-oxo-benzimidazole, and a compound as above which is 5-trifluoromethyl-2,3-dihydro-1-(5-phenyl-2-hydroxyphenyl)-1H-2-oxo-benzimidazole, and a compound as above which is 5-trifluoromethyl-6-nitro-2,3-dihydro-1-(3-nitro-5-chloro-2-hydroxyphenyl)-1H-2-oxo-benzimidazole, further a method of treating a disease in a mammal, including a human, responsive to opening of potassium channels, which comprises administering to a mammal in need thereof an effective amount of a compound as first above indicated, and a method as above wherein hypertension, asthma, ischemia or convulsions are treated, and a method as above wherein the compound is administered in the form of a pharmaceutical composition thereof, in which it is present together with a pharmaceutically-acceptable carrier or diluent, and further a pharmaceutical composition comprising a therapeutically-effective amount of a compound as first above together with a pharmaceutically-acceptable carrier, and further a method of preparing a compound as first above which comprises the step of reacting a compound having the formula

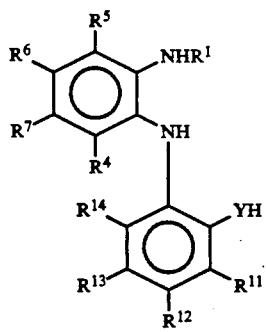

wherein $R^1$, $R^4$, $R^5$, $R^6$, $R^7$, Y, $R^{11}$, $R^{12}$, $R^{13}$ and $R^{14}$ have the meanings set forth above with phosgene, a urea derivative, thiocarbonyl diimidazol, or N-cyanoimido-S,S'-dimethyldithiocarbonate.

BIOLOGICAL ACTIVITY

The compounds of the present invention are potent openers of the high conductance, calcium-activated K+-channel, sometimes referred to as the Big K+ channel or the $BK_{Ca}$ channel. The $BK_{Ca}$ channel is present in most neuronal cells, in airway and vascular smooth muscle cells, as well as in pancreatic β-cells.

The ability of the compounds of the present invention to open the $BK_{Ca}$ channel can be demonstrated in several ways.

All experiments were performed with patch-clamp technique (Hamill et al., Pflügers Arch. 391, 85–100 (1981). The ion composition of the internal solution was (in mM) 4 NaCl, 140 KCl, 1 $CaCl_2$, 1 $MgCl_2$, 2 EGTA, 10 HEPES and the external solution contained 140 NaCl, 4 KCl, 2 $CaCl_2$, 1 $MgCl_2$ and 10 HEPES.

WHOLE CELL RECORDINGS

The membrane potential of N1E-115 neuroblastoma cells was determined in whole-cell recordings using current clamp mode (HEKA EPC-9 patch-clamp amplifier) Due to the high-resistance seal and the large size of these cells, the recorded membrane potential stayed stable for periods of 30–60 min, although at somewhat depolarized values (−15–−60 Mv).

Administration of for example 1-(5-chloro-2-hydroxyphenyl)-5-trifluoromethyl-1,3-dihydro-2H-benzimidazol-2-one (30 μM) to the bath hyperpolarized the cells after a delay of 1–3 min. The average hyperpolarization was −14 Mv (SD=−5 Mv, n=8), and the effect was largest in the cells being most depolarized prior to administration of the compound The equilibrium potentials for K+, Cl−, and Na+ in these experiments were −90 mV, 0 mV, and +90 mV, respectively (cf. ion composition above) Thus, since potassium is the only ion having a reversal potential more negative than the resting membrane potential, the observed hyperpolarization induced by the test compound must be explained through an increased potassium conductance.

SINGLE CHANNEL EXPERIMENTS

In inside-out patches of cerebellar granule cell membrane single $BK_{Ca}$ channels were activated by for example 5-trifluoromethyl-1-(5-chloro-2-hydroxyphenyl)-1,3-dihydro-2H-benzimidazole-2-one (3–10 μM), 5-trifluoromethyl-1-(2-hydroxyphenyl)-1,3-dihydro-2H-benzimidazole-2-one (10-30 mM), 5-trifluoromethyl-1-(5-phenyl-2-hydroxyphenyl)-1,3-dihydro-2H-benzimidazole-2-one (3–30 μM). All compounds increased the open probability of the $BK_{Ca}$. channel by several hundred percent. No effect was found on the delayed rectifier K+ channel or on the Cl− channels also present in the patches.

The $BK_{Ca}$ channel in granule cells has been studied in symmetric 144 mM K+, and under these conditions the average conductance is 154 pS (76 pS with 4 mM external K+). Charybdotoxin blocks the channel in outside-out patches with the characteristic blocking pattern of silent periods interdispersed with periods of low or normal activity, thus confirming the identity of the channel activated by the compounds of the invention.

Likewise, in cultured bovine aortic smooth muscle cells in which the $BK_{Ca}$. is the predominant K+ channel, for example 1,3-dihydro-1-(5-chloro-2-hydroxyphenyl)-5,6-dichloro-2H-benzimidazole-2-one (3–30 μM), 1,3-dihydro-1-(3-hydroxy-2-naphthyl)-5-trifluoromethyl-2H-benzimidazole-2-one (3–30 μM), 5-trifluoromethyl-1-(5-chloro-2-hydroxyphenyl)-1,3-dihydro-2H-benzimidazole-2-one (3-30 μM), 5-trifluoromethyl-1,3-dihydro-1-(2-hydroxy-5-phenylphenyl)-2H-benzimidazole-2-one (3–30 μM), 1,3-dihydro-1-(3-nitro-5-chloro-2-hydroxyphenyl)-5-trifluoromethyl-6-nitro-2H-benzimidazole-2-one (1–3 μM), and 1,3-dihydro-1-(2-hydroxyphenyl)-5-trifluoromethyl-2H-benzimidazole-2-thion (3–30 μM) significantly activated the $BK_{Ca}$ channel.

Likewise,in cultured guinea pig tracheal smooth muscle cells in which a 160–180 pS $BK_{Ca}$ channel is expressed, for example 1,3-dihydro-1-(5-chloro-2-hydroxyphenyl)-5-trifluoromethyl-2H-benzimidazole-2-one potently activated the $BK_{Ca}$ channel.

PHARMACEUTICAL COMPOSITIONS

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredients or, more broadly, 0.1 to one hundred (100) milligrams, per tablet, are accordingly suitable representative unit dosage forms.

METHOD OF TREATING

The compounds of this invention are extremely useful in the treatment of disorders of mammals due to their potent potassium channel activating properties. These properties make the compounds of this invention extremely useful in the treatment of convulsions, asthma, hypertension, ischemia, and other disorders sensitive to potassium channel activating activity. The compounds of this invention may accordingly be administered to a subject, including a human, in need of treatment, alleviation, or elimination of an indication associated with the potassium channels. This includes especially convulsions and every form of epilepsia, asthma, hypertension and ischemia.

Suitable dosage ranges are 0.1-1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

EXAMPLE 1 a) N-(2-hydroxyphenyl)-2-nitroaniline

A solution of 2-nitrofluorobenzene (2 g, 20 mmol), 2-aminophenol (2.2 g, 20 mole) and triethylamine (2.8 ml) in tetrahydrofuran was stirred for 16 hours at 100° C. and then for 48 hours at RT. The reaction mixture was then poured onto a mixture of 50 ml water and 50 ml hexane. The phases were separated and the aqueous phase was extracted with ether. The obtained organic solution was extracted with 20 ml 2 N sodium hydroxide. The aqueous phase was neutralized and acidified with hydrochloric acid. The precipitate was extracted with ether which was dried with MgSO$_4$. The organic solution was evaporated to give an orange oil which crystallized over a short period. Yield 0.6 g, of the title compound, M.p. 132°-134° C. The following compounds were prepared in a similar manner.

N-(4-hydroxyphenyl)-2-nitroaniline, M.p. oil at RT, by reaction between 2-fluoro-nitrobenzene and 4-aminophenol.

N-(3-hydroxyphenyl)-2-nitroaniline, M.p. 128°-129° C., by reaction between 2-fluoro-nitrobenzene and 3-aminophenol.

N-(2-hydroxyphenyl)-2-nitro-4,6-dichloro-aniline, M.p. 182°-184° C., by reaction between 2,3,5-trichloro-nitrobenzene and 2-aminophenol.

N-(2-hydroxyphenyl)-2-nitro-4-trifluoromethyl-aniline, M.p. oil at RT, by reaction between 2-aminophenol and 2-chloro-5-trifluoromethyl-nitrobenzene.

N-(2-methoxy-5-chloro-phenyl)-2-nitroaniline, M.p. 107°-108° C., by reaction between 2-fluoro-nitrobenzene and 2-methoxy-5-chloro-aniline.

N-(2-methoxy-5-chloro-phenyl)-4-trifluoromethyl-2-nitroaniline, M.p. 133°-136° C., by reaction between 2-chloro-5-trifluoromethyl-nitrobenzene and 2-methoxy-5-chloro-aniline.

N-(2-methoxy-5-chlorophenyl)-2-nitro-4,6-dichloroaniline, M.p. 60°-61° C., by reaction between 2,3,5-trichloro-nitrobenzene and 2-methoxy-5-chloro-aniline.

N-(2-methoxyphenyl)-2-nitroaniline, M.p. 80°-82° C. by reaction between 2-methoxyaniline and 2-fluoro-nitrobenzene.

N-2-nitrophenyl-o-phenylendiamine, M.p. 95°-98° C. by reaction between o-phenylendiamine and 2-fluoronitrobenzene.

b) N-(2-methoxy-4-phenylphenyl)-2-nitroaniline

To a stirred solution of 2-fluoronitrobenzene (10 mmol, 1 ml) and 2-methoxy TM 4-phenylaniline (10 mmol, 2.0 g) in tetrahydrofuran (50 ml) was added sodium hydride (10 mmol, 380 mg-60% in mineral oil). The reaction mixture was stirred at reflux temperature for 8 hours and then evaporated in vacuo. The residue was partitioned between ether (100 ml) and 1N hydrochloric acid (50 ml). The organic phase was dried and evaporated in vacuo. The residue was extracted several times at room temperature with petrol ether, in order to remove remaining 2-fluoronitrobenzene. This treatment left the title compound as a dark yellow oil.

The following compounds were prepared in a similar manner.

N-(2-methoxyphenyl)-2-nitro-4-trifluoromethyl aniline, M.p. 112°-114° C. by reaction between o-anisidine and 4-chloro-3-nitro-benzotrifluoride.

N-(2-methoxy-5-trifluoromethylphenyl)-2-nitro-4-trifluoromethyl aniline, M.p 90°-95° C. by reaction between 3-amino-4-methoxybenzotrifluoride and 4-chloro-3-nitrobenzotrifluoride.

N-(2-methoxyphenyl)-2-nitro-4-dimethylsulfamoyl-aniline, M.p. 136°-138° C., by reaction between 2-methoxy-aniline and 5-dimethylsulfamoyl-2-chloronitrobenzene.

N-(2-methoxyphenyl)-2-nitro-4,5-dichloroaniline, M.p. 145°-148° C., by reaction between 2-methoxyaniline and 2-fluoro-4,5-dichloronitrobenzene.

N-(3-hydroxy-2-naphthyl)-2-nitro-4-trifluoromethyl-aniline, by reaction between 3-hydroxy-2-aminonaphthalene and 2-chloro-5-trifluoromethyl-nitrobenzene.

N-(2-hydroxy-1-naphthyl)-2-nitro-4-trifluoromethyl-aniline, M.p. 187°-190° C., by reaction between 2-chloro-5-trifluoromethyl-nitrobenzene and 2-hydroxy.1-amino-naphthalene.

N-(5-chloro-2-methoxyphenyl)-2-nitro-4-methoxyaniline, M.p. 112°-114° C., by reaction between 2-methoxy-5-chloroaniline and 2-nitro-4-methoxychlorobenzene.

N-(2-methoxyphenyl)-2-nitro-4-trifluoromethyl-5-chloroaniline, M.p. 142°-145° C., by reaction between 2-methoxyaniline and 2-chloro-4-chloro-5-trifluoromethyl-nitrobenzene.

c) 4,5-dichloro-2-nitro-N-(2-hydroxyphenyl)aniline, M.p. 193°-194° C.

A solution of 4,5-dichloro-2-fluoro-nitrobenzene (2.1 g, 10 mmol) and o-aminophenol (2.1 g, 19 mmol) in a mixture of dimethylformamide (25 ml) and pyridine was stirred overnight at 60° C. The solvents were evaporated, and the residue was partitioned between ether (100 ml)/1N Hcl (100 ml). The organic phase was washed with water, dried and evaporated This gave a crystalline residue of the crude product, which was recrystallized in methanol, M.p. 193°-194° C.

In a similar manner the following compound was prepared:

2-nitro-4-dimethylsulfamoyl-N-(5-chloro-2-hydroxyphenyl)-aniline, oil at RT, by reacting 2-chloro-5-dimethylsulfamoyl-nitrobenzene and 2-amino-4-chlorophenol.

EXAMPLE 2 a) 2-benzoxazolinone 1.09 g 2-aminophenol was dissolved in dry tetrahydrofuran (25 ml) and triethylamine (3.09 g). Then phosgene (5.5 ml) was added dropwise and the resulting mixture was refluxed for 4 hours and was left at RT overnight. The reaction mixture was filtrated and the filtrate was evaporated. Yield 0.75 g of title compound, M.p. 137°-138° C.

The following compounds were prepared in a similar manner.
5-chloro-2-benzoxazolinone, M.p. 190°–192° C.
5-nitro-2-benzoxazolinone, M.p. 207°–210° C.

b) 5-amino-2-benzoxazolinone, M.p. 205°–210° C.

The compound was obtained after reduction of 5-nitro-2-benzoxazolinone under standard conditions using 5% Pd/C. as catalyst and ethanol as solvent.

c) 5-acetamino-2-benzoxazolinone

To a stirred suspension of 5-amino-2-benzoxazolinone (3.39 g, 22.5 mmol) and triethylamine (3.17 ml, 22.5 mmol) in dry tetrahydrofuran (50 ml) was dropwise added acetylchloride (1.6 ml, 22.6 mmol). The reaction mixture was stirred for additional 2 hours at room temperature, whereafter the precipitate was filtered off The crystals were treated with water (100 ml), filtered off and washed with water. This treatment left the product as white crystals, M.p. 295°–300° C.

d) N-(2-nitrophenyl)-2-benzoxazolinone 0.7 g of 2-benzoxazolinone was dissolved in 5 ml of dimethylformamide and 0.52 ml 2-fluoro-nitrobenzene was added. Then 0.27 g sodium hydride (60% oil suspension) was added. The mixture was stirred at RT until gas development ceased and thereafter at 80° C. for 1 hour. The reaction mixture was cooled and poured unto 25 ml water and 1 ml glacial acetic acid. The precipitate was filtered of and was washed with water and diethyl ether. Yield 1.0 g of the title compound, M.p. 153°–155° C.

The following compounds were prepared in a similar manner.

N-(2-nitro-4-trifluoromethylphenyl)-5-chloro-2-benzoxazolinone, M.p. 177°–179° C. by reaction between 2-chloro-5-trifluoro-nitrobenzene and 5-chloro-2-benzoxazolinone.

5-acetamino-N-(2-nitro-4-trifluoromethylphenyl)-2-benzoxazolinone, M.p. 215°–217° C. by reaction between 5-acetamino-2-benzoxazolinone and 4-chloro-3-nitro benzotrifluoride.

N-(2-nitrophenyl)-2-benzothiazolinone, M.p. 92°–95° C. by reaction between 2-fluoronitrobenzene and 2-benzothiazolinone.

N-(2-nitro-4-fluorophenyl)-5-chloro-2-benzoxazolinone by reaction between 2,4-difluoro-nitrobenzene and 5-chloro-2-benzoxazolinone. The product was used without further purification.

N-(2-nitro-4-trifluoromethylphenyl)-5-phenyl-o-anisidine by reaction between 2-fluoro-5-trifluoromethyl-nitrobenzene and 5-phenyl-o-anisidine. The product was used without further purification.

N-(2-nitro-4-trifluoromethyl-5-chlorophenyl)-5-phenyl-o-anisidine by reaction between 2-chloro-4-chloro-5-trifluoromethyl-nitrobenzene and 5-phenyl-o-anisidine. The product was used without further purification.

N-(2-nitrophenyl)-3,5-dichloro-2-methoxy-aniline by reaction between 2-fluoro-nitrobenzene and 3,5-dichloro-o-anisidine, brown crystals, M.p. 104°–105° C.

N-(2-nitro-4-benzoylphenyl)-5-chloro-2-benzoxazolinone by reaction between 4-chloro-3-nitrobenzophenone and 5-chloro-2-benzoxazolinone. The product was used without further purification.

N-(2,4-dinitrophenyl)-5-chloro-2-benzoxazolinone by reaction between 2,4-dinitro-chlorobenzene and 5-chloro-2-benzoxazolinone. The product was used without further purification.

e) N-(2-hydroxyphenyl)-2-nitro-aniline 0.23 g N-(2-nitrophenyl)-2-benzoxazolinone was heated at 70° C. for 1 hour in a mixture of 2 ml 4N sodium hydroxide and 5 ml 96% ethanol. The reaction mixture was then cooled and neutralized with hydrochloric acid. The red precipitate was isolated by filtration or extraction with diethyl ether followed by evaporation. Yield 180 mg title compound, M.p. 133°–135° C.

The following compounds were prepared in a similar manner.

2-nitro-N-(5-chloro-2-hydroxyphenyl)-4-trifluoromethyl aniline, M.p. 67°–70° C. from N-(2-nitro-4-trifluoromethylphenyl)-5-chloro-2-benzoxazolinone.

N-(5-acetamido-2-hydroxyphenyl)-2-nitro-4-trifluoromethyl aniline, M.p. 205°–210° C. from N-(2-nitro-4-trifluoromethylphenyl)-5-acetamido-2-benzoxazolinone.

N-(2-mercaptophenyl)-2-nitroaniline, M.p. 105°–110° C. from N-(2-nitrophenyl)-2-benzothiazolinone.

N-(5-chloro-2-hydroxyphenyl)-4-fluoro-2-nitro-aniline from N-(2-nitro-4-fluorophenyl)-5-chloro-2-benzoxazolinone. The product was used without further purification.

N-(5-chloro-2-hydroxyphenyl)-4-benzoyl-2-nitro-aniline from N-(2-nitro-4-benzoylphenyl)-5-chloro-2-benzoxazolinone. The product was used without further purification.

N-(5-chloro-2-hydroxyphenyl)-2,4-dinitroaniline from N-(2,4-dinitrophenyl)-5-chloro-2-benzoxazolinone. The product was used without further purification.

EXAMPLE 3

2-amino-N-(5-chloro-2-hydroxyphenyl)-4-nitro-anilinehydrochloride

A mixture of N-(5-chloro-2-hydroxyphenyl)-2,4-dinitroaniline (7.9 g, 25.6 mmol), ammoniumchloride (5,2 g, 98 mmol) and sodiumsulfide nonahydrate (23.5 g, 98 mmol) in methanol (350 ml; was refluxed for one hour. The reaction was filtered after cooling to room temperature and the filtrate was concentrated in vacuo. The remanecens was dissolved in ethanol, acidified with concentrated hydrochloric acid and the mixture was concentrated in vacuo. Finally the crude product was triturated with diethyl ether yielding the title compound as red/brown crystals. The product was used without further purification.

EXAMPLE 4

N-(2-hydroxyphenyl)-2-phenylene diamine hydrochloride 1.5 g of N-(2-hydroxyphenyl)-2-nitroaniline was hydrogenated under standard conditions (1 atm) with 0.5 g 5% pd/C. as catalyst, ethanol (100 ml) as solvent and 0 6 ml concentrated hydrochloric acid to give the title compound as an oil which crystallized over a short period. Yield: 1.1 g greenish crystals of the title compound, M.p. 220°–223° C.

The following compounds were prepared in a similar manner. In cases where the free bases were isolated, addition of hydrochloric acid were omitted during the hydrogenation.

N-(2-methoxyphenyl)-2-amino-4-trifluoroaniline, hydrochloride, M.p. 258°–260° C.

2-amino-N-(2-hydroxyphenyl)-4-trifluoromethyl aniline, M.p. 108°–109° C.
2-amino-N-(2-methoxy-5-chloro-phenyl)-aniline, M.p. oil at RT. Raney Nickel was used as catalyst.
2-amino-4-trifluoromethyl-N-(2-methoxy-5-chlorophenyl)-aniline, M.p. oil at RT. Raney nickel was used as catalyst.
2-amino-N-(2-methoxyphenyl)-aniline, M.p. Oil at RT.
2-amino-4,6-dichloro-N-(2-methoxy-5-chlorophenyl)-aniline, M.p. Oil at RT. Raney Nickel was used as catalyst.
N-(4-hydroxyphenyl)-2-amino-aniline, M.p. oil at RT.
N-(3-hydroxyphenyl)-2-amino-aniline, M.p oil at RT.
2-amino-N-(5-chloro-2-hydroxyphenyl)-4-trifluoromethyl anilinehydrochloride, M.p. 192°–195° C. Raney Nickel was used as catalyst.
N-(2-methoxy-5-phenylphenyl)-2-amino aniline, hydrochloride, oil at RT.
N-(2-hydroxyphenyl)-4,5-dichloro-2-amino aniline, M.p. 132°–133° C. Raney nickel was used as catalyst.
N-(5-acetamino-2-hydroxyphenyl)-4-trifluoromethyl-2-amino aniline, M.p. 185°–190° C.
N-(2-mercaptophenyl)-2-amino aniline, oil at RT.
2-(2-amino-4-trifluoromethylphenyl)amino-3-hydroxypyridine, M.p. 160°–165° C.
N-(5-chloro-2-methoxyphenyl)-2-amino aniline. Raney nickel was used as catalyst, oil at RT.
N-(5-chloro-2-methylphenyl)-2-amino-4-methoxy-aniline, M.p. oil at RT. Raney nickel was used as catalyst.
N-(5-chloro-2-hydroxyphenyl)-2-amino-4-dimethylsulfamoyl-aniline, M.p. 207°–209° C. Raney nickel was used as catalyst.
N-(2-methoxyphenyl)-2-amino-4-dimethylsulfamoyl-aniline, M.p. 162°–164° C. 5% Pd/C. was used as catalyst
N-(2-methoxyphenyl)-2-amino-4-trifluoromethyl-5-chloro-aniline, M.p. 188°–190° C. Raney nickel was used as catalyst.
N-(2-methoxyphenyl)-2-amino-4,5-dichloro-aniline, hydrochloride, M.p. 176°–178° C. Raney nickel was used as catalyst
N-(3-hydroxy-2-naphthyl)-2-amino-4-trifluoromethyl-aniline, M.p. 280° C. (decomp.). 5% Pd/C. was used as catalyst.
N-(2-hydroxy-1-naphthyl)-2-amino-4-trifluoromethyl-aniline, M.p. 154°–157° C. 5% Pd/C. was used as catalyst.
2-amino-N-(5-chloro-2-hydroxyphenyl)-4-fluoro-anilinehydrochloride, Raney Nickel was used as catalyst. The product was used without further purification.
2-amino-N-(5-phenyl-2-methoxyphenyl)-4-trifluoromethyl-aniline, 5% Pd/C. was used as catalyst. The product was used without further purification.
2-amino-N-(5-phenyl-2-methoxyphenyl)-5-chloro-4-trifluoromethyl-aniline, Raney Nickel was used as catalyst. The product was used without further purification.
2-amino-N-(3,5-dichloro-2-methoxyphenyl)-aniline, hydrochloride, Raney Nickel was used as catalyst. Grey crystals, M.p. 191°–192° C.
2-amino-N-(5-chloro-2-hydroxyphenyl)-4-benzoyl-aniline, Raney Nickel was used as catalyst. The product was used without further purification.

EXAMPLE 5

1,3-dihydro-1-(2-hydroxyphenyl)-2H-benzimidazol-2-one 2-amino-N-(2-hydroxyphenyl)-aniline (1 g, 4.2 mmol) and 2.1 ml (15 mmol) triethylamine were dissolved in dry tetrahydrofuran (50 ml). Then 2.5 ml (5 mM in toluene) of phosgene was added dropwise, whereafter the mixture was refluxed for 2 hours. The resulting mixture was evaporated in vacuo and the residue was partitioned between water and ethyl acetate. The organic phase was extracted with a 1 N sodium hydroxide solution (20 ml) The aqueous phase was neutralized whereafter the crude product was isolated by filtration The product was recrystallized from 15 ml isopropanol Yield: 0.5 g of the title compound, M.p 216–217 mg.

In a similar way the following compounds were synthesized
5-trifluoromethyl-1,3-dihydro-1-(2-hydroxyphenyl)-2H-benzimidazol-2-one, M.p. 154°–155° C.
1-(5-chloro-2-hydroxyphenyl)-5-trifluoromethyl-1,3-dihydro-2H-benzimidazol-2-one, M.p. 223°–224° C.
1,3-dihydro-1-(3-hydroxyphenyl)-2H-benzimidazol-2-one, M.p. 248°–250° C.
1,3-dihydro-1-(2-methoxyphenyl)-2H-benzimidazol-2-one, M.p. 184°–186° C.
1-(5-chloro-2-methoxyphenyl)-5-trifluoromethyl-1,3-dihydro-2H-benzimidazol-2-one, M.p. 135°–138° C.
1-(5-chloro-2-methoxyphenyl)-1,3-dihydro-2H-benzimidazol-2-one, M.p. 168°–170° C.
1-(5-chloro-2-methoxyphenyl)-5,7-dichloro-1,3-dihydro-2H-benzimidazol- 2-one, M.p. 218°–220° C.
1,3-dihydro-1-(2-methoxyphenyl)-5-trifluoromethyl-2H-benzimidazol-2-one, M.p. 223°–226° C.
1-(5-acetamino-2-hydroxyphenyl)-1,3-dihydro-5-trifluoromethyl-2H-benzimidazol-2-one, M.p. 180°–185° C.
1,3-dihydro-1-(2-mercaptophenyl)-2H-benzimidazol-2-one, M.p. 90°–195° C.
1,3-dihydro-1-(2-methoxy-5-phenylphenyl)-2H-benzimidazol-2-one, M.p. rearranges at 115° C. melts at 185° C.
5,6-dichloro-1,3-dihydro-1-(2-hydroxyphenyl)-2H-benzimidazol-2one, M.p. 282°–285° C.
1,3-dihydro-(5-chloro-2-methoxyphenyl)-5-methoxy-2H-benzimidazol-2-one, M.p. 199°–202° C.
1,3-dihydro-1-(5-chloro-2-hydroxyphenyl)-5-dimethylsulfamoyl-2H-benzimidazol-2-one, M.p. 100°–105° C. (decomp.).
1,3-dihydro-1-(2-methoxyphenyl)-5-dimethylsulfamoyl-2H-benzimidazol-2-one, M.p. 200°–203° C.
1,3-dihydro-1-(2-methoxyphenyl)-5-trifluoromethyl-6-chloro-2H-benzimidazol-2-one, M.p. 289°–291° C.
1,3-dihydro-1-(2-methoxyphenyl)-5,6-dichloro-2H-benzimidazol-2-one, M p. 262°–264° C.
1,3-dihydro-1-(3-hydroxy-2-naphthyl)-5-trifluoromethyl-2H-benzimidazol-2-one, M.p. 290°–293° C.
1,3-dihydro-1-(2-hydroxy-1-naphthyl)-5-trifluoromethyl-2H-imidazole-2-one, M.p. 223°–228° C.

EXAMPLE 6

1-(5-chloro-2-hydroxyphenyl)-1,3-dihydro-2H-benzimidazol-2-one 1-(5-chloro-2-methoxyphenyl)-1,3-dihydro-2H-benzimidazol-2-one (0.3 g) was refluxed for 32 hours in 48% HBr (1 ml) in acetic acid (5 ml). The reaction mixture was then cooled and 25 ml water was added, whereby the crude product precipitated. To the mixture was added 5 ml diethylether whereafter it was filtered to give 150 mg of the title compound, M.p. 248°–250° C.

The following compounds were prepared in a similar manner from the corresponding alkoxy analogues:

1,3-dihydro-1-(2-hydroxy-5-phenylphenyl)-2H-benzimidazol-2-one, M.p. 130° C. decomp.

5,7-dichloro-1-(5-chloro-2-hydroxyphenyl)-1,3-dihydro-2H-benzimidazol-2-one, M p. 206°–208° C.

EXAMPLE 7

1,3-dihydro-1-(2-hydroxyphenyl)-4-hydroxy-2H-benzimidazol-2-one

A slurry of 1,3-dihydro-1-(2-methoxyphenyl)-4-methoxy-2H-benzimidazol-2-one (500 mg, 1.9 mmol) in 15 ml absolute methylene chloride under a nitrogen atmosphere at −78° C., was added boron tribromide (350 μl, 3.7 mmol) and the mixture was allowed to reach room temperature. After stirring for 5 hours the mixture was poured unto 150 ml water and was stirred vigorously for 15 minutes The phases were separated, the water phase was extracted twice with 50 ml methylene chloride and the combined organic phases were dried and concentrated in vacuo. The crude crystalline product was triturated with a small amount of ethyl acetate yielding the title compound as slightly brown crystals, M.p. 235° C. (dec.).

The following compounds were prepared in a similar manner.

1,3-dihydro-1-(5-phenyl-2-hydroxyphenyl)-5-trifluoromethyl-2H-benzimidazol-2-one, white crystals M.p. 258°–259° C.

1,3-dihydro-1-(5-phenyl-2-hydroxyphenyl)-5-trifluoromethyl-6-chloro-2H-benzimidazol-2-one, white crystals M.p. 275°–277° C.

1,3-dihydro-1-(3,5-dichloro-2-hydroxyphenyl)-2H-benzimidazol-2-one, light grey crystals, M.p. 238°–239° C.

EXAMPLE 8

1,3-dihydro-1-(5-chloro-2-hydroxyphenyl)-5-trifluoromethyl-2H-benzimidazol-2-thione.

2-amino-N-(5-chloro-2-hydroxyphenyl)-4-trifluoromethyl-aniline (0.51 g, 1 5 mmol), triethylamine (0.28 ml, 2 mmol) and thiocarbonyl diimidazol (0.36 g, 2 mmol) was dissolved in dry tetrahydrofuran (15 ml) and the mixture was stirred for 30 minutes. The reaction mixture was evaporated in vacuo. The residue was redissolved in ethanol and water and light petroleum were added. The precipitate was isolated and was purified by column chromatography on silica gel with ether/light petroleum (2:1) as eluent. Yield of title compound was 200 mg, M.p. 248°–250° C.

The following compounds were prepared in a similar manner.

1,3-dihydro-1-(5-chloro-2-methoxyphenyl)-5-trifluoromethyl-2H-benzimidazol-2-thione, M.p. 168°–170° C.

1,3-dihydro-1-(3-hydroxy-2-naphthyl)-5-trifluoromethyl-2H-benzimidazol-2-thione, M.p. 216°–220° C.

EXAMPLE 9

1,3-dihydro-1-(5-chloro-2-methoxyphenyl)-5-trifluoromethyl-2H-2-cyanoimido-benzimidazole N-(5-chloro-2-methoxyphenyl)-2-amino-4-trifluoromethyl-aniline hydrochloride (1.06 g, 3 mmol), N-cyanoimido-S,S'-dimethyl-dithiocarbonate (0.44 g, 3 mmol) and 60% sodiumhydride in oil (0.24 g, 6 mmol) was mixed in dry tetrahydrofuran (15 ml) and was stirred at RT. The reaction mixture was evaporated and dimethylformamide (10 ml) was added to the residue and the resulting mixture was heated at 80° C. for 24 hours, whereafter 6 mmol additional sodium hydride was added and heating was continued for 24 hours. Thereafter water and light petroleum was added The precipitate was filtrated off and was redissolved in ether. The solution was evaporated and the residue was treated with light petroleum and thereafter with toluene Yield: 100 mg of the title compound, M.p. 218°–220° C.

EXAMPLE 10

1,3-dihydro-1-(5-chloro-2-hydroxyphenyl)-5-fluoro-2H-benzimidazol-2-one

A mixture of 2-amino-N-(5-chloro-2-hydroxyphenyl)-5-fluoroanilinehydrochloride (14 mmol) and urea (1.2 g, 20 mmol) in 50 ml absolute dimethylethyleneglycol was stirred at 170° C. for 4 hours The mixture was, after cooling to ambient temperature, poured unto 200 ml ice water and a crystalline product was isolated by filtration. The crude product was treated with active coal in ethanol and recrystallized from toluene to yield the title compound as white crystals, M.p. 256°–260° C.

The following compounds were prepared in a similar manner.

1,3-dihydro-1-(5-phenyl-2-methoxyphenyl)-5-trifluoromethyl-2H-benzimidazol-2-one, white crystals after column chromatography using methylene chloride:methanol (9:1) as eluent, M.p. 258°–259° C.

1,3-dihydro-1-(5-phenyl-2-methoxyphenyl)-5-trifluoromethyl-6-chloro-2H-benzimidazol-2-one, white crystals, M.p. 295°–298° C.

1,3-dihydro-1-(5-chloro-2-hydroxyphenyl)-5-benzoyl-2H-benzimidazol-2-one, White crystals, M p 279°–280° C.

EXAMPLE 11

2-ethoxycarbonylamino-N-(3,5-dichloro-2-methoxyphenyl)-aniline.

To a mixture of 2-Amino-N-(3,5-dichloro-2-methoxyphenyl)-aniline (2.23 g, 6.3 mmol) and triethylamine (1.74 ml 12.5 mmol) in absolute methylene chloride (40 ml) was at room temperature added ethyl chloroformate (1.2 ml, 13.8 mmol) and the mixture was refluxed over night. The reaction mixture was allowed to reach room temperature and was diluted with water (40 ml) and the water phase was extracted twice with diethylether. The combined organic phases were dried and concentrated in vacuo yielding a red/brown oil which was used without further purification.

The following compounds were prepared in a similar manner.

2-ethoxycarbonylamino-N-(5-chloro-2-hydroxyphenyl)-4-nitroaniline, brown crystals. The product was used without further purification.

EXAMPLE 12

1,3-dihydro-1-(3,5-dichloro-2-methoxyphenyl)-2H-benzimidazol-2-one

To a solution of 2-ethoxycarbonylamino-N-(3,5-dichloro-2-methoxyphenyl)-aniline (1.94 g, 5 4 mmol) in absolute ethanol (20 ml) was at room temperature added small pieces of sodium (0.25 g, 10.8 mmol) The mixture was heated at reflux for 1½ hours after all the sodium has reacted The mixture was after cooling to room temperature poured into ice water (50 ml) and after stirring for 15 minutes the crystalline product was collected by filtration yielding the title compound as slightly pink crystals, M.p. 202°–203° C.

The following compound was prepared in a similar manner.

1,3-dihydro-1-(5-chloro-2-hydroxyphenyl)-2H-5-nitrobenzimidazole-2-one, beige crystals, M.p. 238°–239° C.

EXAMPLE 13 a) N,N'-di-(2-methoxyphenyl)-urea

A solution of o-anisidine (12.3 g, 100 mmol) and triethylamine (11 ml, 80 mmol) in absolute toluene (100 ml) was under stirring on an ice bath added phosgene (20.7 ml, 1.93 M sol in toluene, 40 mmol) and the mixture was stirred at 90° C. for 3 hours. The reaction mixture was after cooling to ambient temperature poured into water (100 ml) and the title compound was collected by filtration and used without further purification.

b) 1,3-dihydro-1-(2-methoxyphenyl)-4-methoxy-2H-benzimidazol-2-one

A mixture of N,N'-di-(2-methoxyphenyl)-urea (6.81 g, 25 mmol) and tetra-n-butyl-ammoniumbromide (0.4 g, 1.3 mmol) in methylene chloride/methanol (1:1 , 200 ml) was at room temperature under vigorous stirring added a solution of sodium hydroxide (2 g in 10 ml water) followed by a solution of sodiumhypochlorite(55 ml, *Aldrich*). The mixture was stirred for 4 hours and 30 ml water was added The organic phase was washed with 10 ml 1M hydrogen chloride sol., dried and concentrated in vacuo. Upon trituration with diethyl ether dark grey crystals separated The crude product was recrystallized twice, first from ethanol and then from ethyl acetate yielding the title compound as white crystals, M.p. 246°–247° C.

EXAMPLE 14

1,3-dihydro-1-(5-chloro-2-hydroxyphenyl)-3-methyl-5-fluoro-2H-benzimidazol-2-one A mixture of 1,3-dihydro-1-(5-chloro-2-hydroxyphenyl)-5-fluoro-2H-benzimidazol-2-one (300 mg, 1.1 mmol), anhydrous potassium carbonate (415 mg) and Iodomethane (68 µl) in 10 ml absolute acetone was refluxed for 5 hours. The mixture was filtered, concentrated in vacuo and the crude product was subjected to column chromatography using methylene chloride:acetone (20:1) as eluent. The fraction containing the product was concentrated in vacuo and the title compound was obtained as white crystals, M.p. 247°–250° C.

The following compound was prepared in a similar manner 1,3-dihydro-1-(5-chloro-2-hydroxyphenyl)-3-methyl-5-trifluoromethyl-2H-benzimidazol-2-one, white crystals, M.p. 257°–260° C.

EXAMPLE 15

1,3-dihydro-1-(5-chloro-3-bromo-2-hydroxyphenyl)-5-trifluoromethyl-2H-benzimidazol-2-one A solution of 1,3-dihydro-1-(5-chloro-2-hydroxyphenyl)-5-trifluoromethyl-2H-benzimidazol-2-one (0.2 g, 0.6 mmol) in glacial acetic acid (5 ml) at room temperature was added bromine (45 µl, 0.9 mmol) and, after stirring for 20 minutes, the mixture was poured into water (25 ml). The crude product was collected by filtration, taken up in hot ethanol and precipitated by addition of water yielding the title compound as white crystals, M.p. 254°–255° C.

EXAMPLE 16

1,3-dihydro-1-(5-chloro-3-bromo-2-hydroxyphenyl)-5-trifluoromethyl-6-nitro-2H-benzimidazol-2-one To a slurry of 1,3-dihydro-1-(5-chloro-3-bromo-2-hydroxyphenyl)-5-trifluoromethyl-2H-benzimidazol-2-one (1 g, 2.5 mmol) in glacial acetic acid (5 ml) was under stirring on an ice bath added acetic anhydride (2.5 ml) and two drops of concentrated sulfuric acid. When the starting material had gone into solution, an ice cold solution of potassium nitrate (0.3 g, 3 mmol) in concentrated sulfuric acid (1 ml) was added, and the mixture was stirred for 15 minutes. The reaction mixture was poured into water, the crystalline product was collected by filtration and the acetate was hydrolysed by reflux in ethanol (50 ml) and 4M sodium hydroxide (5 ml) for one hour. The reaction mixture was acidified by addition of 4M hydrochloric acid and water was added until starting precipitation. The mixture was cooled and the crystals were collected by filtration yielding the title compound as slightly yellow crystals, M.p. 262°–264° C.

EXAMPLE 17

1,3-dihydro-1-(5-chloro-3-nitro-2-hydroxyphenyl)-5-trifluoromethyl-2H-benzimidazol-2-one A solution of 1,3-dihydro-1-(5-chloro-2-hydroxyphenyl)-5-trifluoromethyl-2H-benzimidazol-2-one (0.2 g, 0.6 mmol) in concentrated sulfuric acid (2.5 ml) was under stirring on an ice bath added an ice cold solution of potassium nitrate (61 mg, 6 mmol) in concentrated sulfuric acid (1 ml). The reaction mixture was poured onto ice (30 g) and the crude product was collected by filtration and recrystallized from ethanol:water 2:1 yielding the title compound as yellow crystals, M.p. 250° C. (dec.).

The following compounds were prepared in a similar manner.

1,3-dihydro-1-(5-chloro-3-nitro-2-hydroxyphenyl)-5-trifluoromethyl-6-nitro-2H-benzimidazol-2-one, yellow crystals, M.p. 283°–284° C., using two equivalents of potassium nitrate.

1,3-dihydro-1-(3,5-dichloro-2-hydroxyphenyl)-5,6-dinitro-2H-benzimidazol-2-one, yellow crystals, M.p. 300°–303° C., using two equivalents of potassium nitrate.

1,3-dihydro-1-(5-nitro-2-hydroxyphenyl)-5-trifluoromethyl-6-nitro-2H-benzimidazole-2-one, yellow crystals, M.p. 285° C. (decomp.), using two equivalents of potassium nitrate.

EXAMPLE 18

1,3-dihydro-1-(5-chloro-2-hydroxyphenyl)-3-amino-5-trifluoromethyl-2H-benzimidazol-2-one To a solution of 1,3-dihydro-1-(5-chloro-2-hydroxyphenyl)-5-trifluoromethyl-2H-benzimidazol-2-one (0.2 g, 0.6 mmol) in absolute N,N-dimethylformamide (5 ml) was at room temperature added potassium hydroxide (2 pellets) and hydroxylamine-o-sulfonic acid (0.16 g, 1.3 mmol) The reaction was stirred over night, water was added (20 ml) and the mixture was acidified with 4 M hydrochloric acid. The crude crystalline product was collected by filtration and subjected to column chromatography using methylene chloride:methanol (19 1) as eluent. The fractions containing the product were concentrated in vacuo yielding the title compound as white crystals, M.p. 228°–230° C.

We claim:

1. A compound selected from those having the formula

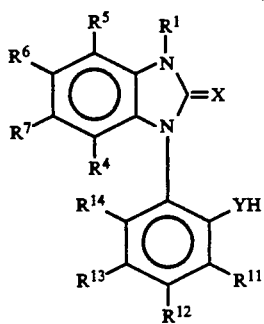

wherein $R^1$ is hydrogen, $NH_2$ or $C_{1-6}$-alkyl which may be branched;

X is O, S, NCN;

Y is O, S;

$R^4$, $R^5$, $R^6$ and $R^7$ independently of each other are hydrogen, halogen, $CF_3$, $NO_2$, $NH_2$, OH, $C_{1-6}$-alkoxy, $C(=O)$-phenyl or $SO_2NR^IR^{II}$ wherein $R^I$ and $R^{II}$ independently are hydrogen or $C_{1-6}$-alkyl;

$R^{11}$ is hydrogen, halogen, $NO_2$ or $SO_2NR'R''$ wherein $R'$ and $R''$ independently are hydrogen or $C_{1-6}$-alkyl;

$R^{13}$ is hydrogen, halogen, phenyl, $CF_3$, $NO_2$;

$R^{12}$ is hydrogen or together with $R^{13}$ forms a $C_{4-7}$-carbocyclic ring which may be aromatic or partially saturated;

$R^{14}$ is hydrogen or together with $R^{13}$ forms a $C_{4-7}$-carbocyclic ring which may be aromatic or partially saturated.

2. A compound of claim 1 which is 5-trifluoromethyl-2,3-dihydro-1-(5-chloro-2-hydroxyphenyl)-1H-2-oxo-benzimidazole.

3. A compound of claim 1 which is 5-trifluoromethyl-2,3-dihydro-1-(5-phenyl-2-hydroxyphenyl)-1H-2-oxo-benzimidazole.

4. A compound of claim 1 which is 5-trifluoromethyl-6-nitro-2,3-dihydro-1-(3-nitro-5-chloro-2-hydroxyphenyl)-1H-2-oxo-benzimidazole.

5. A method of treating a disease in a mammal, responsive to opening of potassium channels, which comprises administering to a mammal in need thereof an effective amount of a compound of claim 1.

6. A method of claim 5 wherein hypertension, asthma, ischemia or convulsions are treated.

7. A method of claim 5 wherein the compound is administered in the form of a pharmaceutical composition thereof, in which it is present together with a pharmaceutically-acceptable carrier or diluent.

8. A pharmaceutical composition comprising a therapeutically-effective amount of a compound of claim 1 together with a pharmaceutically-acceptable carrier.

* * * * *

UNITED STATES PATENT AND TRADEMARK OFFICE
CERTIFICATE OF CORRECTION

PATENT NO. : 5,200,422
DATED : Apr. 6, 1993
INVENTOR(S) : Soren-Peter Olesen, Frank Wätjen It is certified that error appears in the above-identified that said Letters Patent is hereby corrected as shown below:

Title page, [57] ABSTRACT, approximately line 5 (in the formula, left side); change the "$R^7$" (between the "$R^6$ and "$R^4$") to $R^5$, as shown.

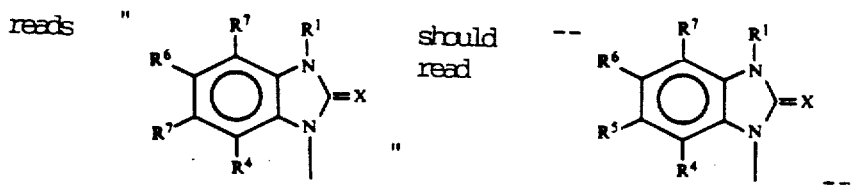

Column 2, approximately lines 1 and 7, (in the formula, top and upper left side);
Column 3, approximately lines 1 and 7, (in the formula, top and upper left side);
Column 15, approximately lines 12 and 17, (in the formula, top and upper left side), in all three instances, change the top "$R^5$" to "$R^7$" and, on the left side of formula, change "$R^7$" to "$R^5$".

UNITED STATES PATENT AND TRADEMARK OFFICE
CERTIFICATE OF CORRECTION

PATENT NO. : 5,200,422

DATED : Apr. 6, 1993

INVENTOR(S) : Soren-Peter Olesen, Frank Wätjen

It is certified that error appears in the above-indentified patent and that said Letters Patent is hereby corrected as shown below:

Column 3, line 66; "-I-" should read -- 1 --.
Column 5, line 64; "2-methoxy TM 4-" should read
    -- 2-methoxy-4- --.
Column 6, lines 30, 31; move the "y" at the beginning of line 31
    to the end of line 30 after "hydrox".
Column 6, line 31; ".1-amino-" should read -- 1-amino- --.
Column 7, line 17; "off The" should read -- off. The --.
Column 7, line 28; "unto" should read -- into --.
Column 7, line 30; "of" should read -- off --.
Column 8, approximately line 41; "5,2 g," should read
    -- 5.2 g, --.
Column 8, line 58; "5% pd/C." should read -- 5% Pd/C --.
Column 8, line 58, 59; "0 6 ml" should read -- 0.6 ml --.
Column 9, line 44; insert a period "." after "catalyst".
Column 10, line 45; "2one," should read -- 2-one, --.
Column 11, line 57; "2H-benzim:idazol-" should read
    -- 2H-benzimidazol- --.
Column 12, line 8; "added The" should read -- added. The --.
Column 12, line 11; "toluene" should read -- toluene. --.
Column 12, line 21; "hours The" should read --hours. The--.
Column 12, line 23; "poured unto 200" should read
    -- poured into 200 --.
Column 12, line 38; "M p" should read -- M. p. --.
Column 12, line 66; "5 4" should read -- 5.4 --.
Column 13, line 2; "reacted The" should read --reacted. The--.
Column 13, line 15; "A" should read -- To a --.
Column 13, line 35; "added The" should read -- added. The --.
Column 13, line 38; "separated The" should read
    -- separated. The --.

UNITED STATES PATENT AND TRADEMARK OFFICE
CERTIFICATE OF CORRECTION

PATENT NO. : 5,200,422
DATED : Apr. 6, 1993
INVENTOR(S) : Soren-Peter Olesen, Frank Wätjen It is certified that error appears in the above-indentified patent and that said Letters Patent is hereby corrected as shown below:

```
Column 13, line 57; "manner" should read -- manner. --.
Column 14, line 34; "A" should read -- To a --.
Column 14, line 68; "mmol) The" should read --mmol). The --.
Column 15, line 4; "(19 1)" should read -- (19:1) --.
Column 16, line 5; "¹²R" should read -- R¹² --.
```

Signed and Sealed this

Tenth Day of May, 1994

BRUCE LEHMAN

*Attest:*

*Attesting Officer*  *Commissioner of Patents and Trademarks*